Figure 1:
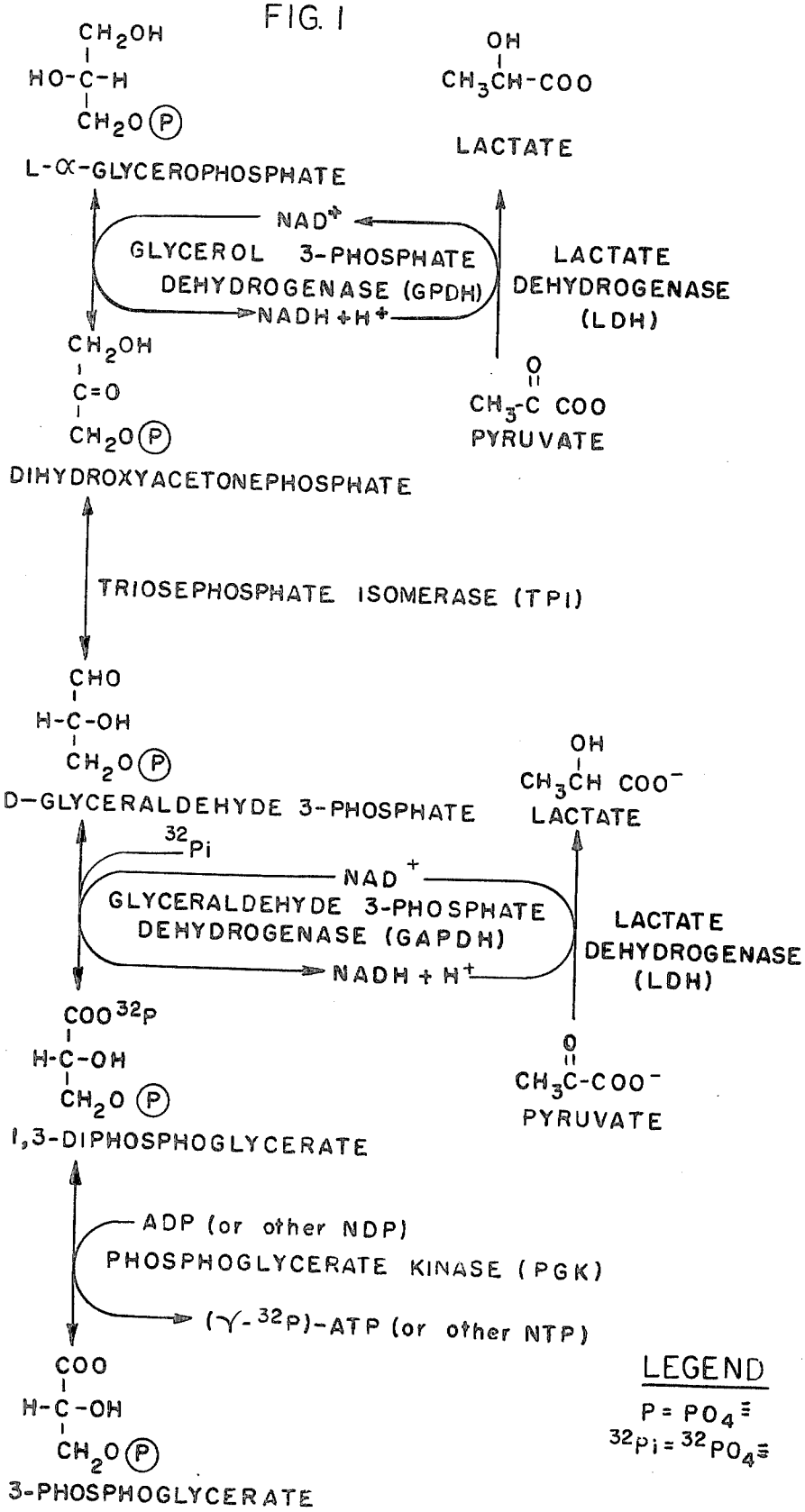

United States Patent [19]

Johnson et al.

[11] 4,209,589

[45] Jun. 24, 1980

[54] ENZYMATIC PROCESS FOR PREPARING [γ-32P]-LABELED NUCLEOTIDES

[75] Inventors: Roger A. Johnson; Timothy F. Walseth, both of Nashville, Tenn.

[73] Assignee: Vanderbilt University, Nashville, Tenn.

[21] Appl. No.: 924,365

[22] Filed: Jul. 13, 1978

[51] Int. Cl.² .............................................. C12D 13/06
[52] U.S. Cl. ........................................ 435/90; 435/92; 435/148; 435/147
[58] Field of Search ........................................ 195/28 N

[56] References Cited

PUBLICATIONS

J. Biol. Chem. 248, 8319–8321 (1973).
Biochem. J. 90 147–149 (1964).

Primary Examiner—Alvin E. Tanenholtz
Attorney, Agent, or Firm—Tilton, Fallon, Lungmus & Chestnut

[57] ABSTRACT

ATP and other nucleoside triphosphates labeled in the γ-phosphate with $^{32}P$ are prepared from L-α-glycerophosphate and their corresponding nucleoside diphosphates by a series of enzymatic reactions in the presence of $NAD^+$, preferably regenerated by lactate dehydrogenase and pyruvate. The resulting [γ-$^{32}P$]nucleotides are useful as reagents for analytical determinations.

16 Claims, 1 Drawing Figure

ENZYMATIC PROCESS FOR PREPARING [γ-$^{32}$P]-LABELED NUCLEOTIDES

GRANT REFERENCE

The invention described herein was made in the course of work under grants AM 07462, AM 18185, and AM 21170 from the United States Public Health Service.

BACKGROUND AND PRIOR ART

Schendel and Wells have disclosed an enzymatic process for preparing [γ-$^{32}$P]-adenosine triphosphate (ATP) with high specific activity. J. Biol. Chem. 248, 8319–8321 (1973). They used D-glyceraldehyde-3-phosphate as the starting material and employed oxidizing dyes for regeneration of NAD+ from NADH. D-glyceraldehyde-3-phosphate is available commercially only as the diethylacetal. For use in the process of Schendel and Wells, the diethylacetal must first be hydrolyzed and removed from the D-glyceraldehyde-3-phosphate. Moreover, unprotected D-glyceraldehyde-3-phosphate tends to be unstable and may have an objectionably short shelf-life.

Oxidizing dyes such as phenazine methosulfate and thiazolyl blue may interfere with subsequent enzyme reactions. For example, where the [γ-$^{32}$P]nucleoside triphosphate is converted by further enzyme reactions to other [$^{32}$P]-labeled nucleotides, such as [α-$^{32}$P]-nucleotides, the intermediate [γ-$^{32}$P]-nucleotide may have to be recovered from the reaction mixture, and then subjected to the additional reactions.

Commercially, the [γ-$^{32}$P]-labeled nucleotides such as [γ-$^{32}$P]-ATP and -dATP have also been prepared by enzymatic processes. However, the products of these processes have not been produced in as high yield and/or as high a specific activity as with the method described herein. Moreover, a more efficient enzymatic system would be very desirable, especially if the process could also be adapted as the first stage of a continuing process for producing other [$^{32}$P]-labeled nucleotides.

SUMMARY OF INVENTION

An enzymatic process is provided using L-α-glycerophosphate (L-α-GP) as the starting material. L-α-GP is stable; the phosphate not being so easily hydrolyzed as is that of D-glyceraldehyde-3-phosphate. Thus, a smaller amount of unlabeled phosphate ($P_i$) is introduced into the reaction mixture. This results in [$^{32}$P]-labeled products of higher specific activity than when D-glyceraldehyde-3-phosphate is used for the starting material, as in the method of Schendel and Wells (cited above). In the process of the present invention, the L-α-GP is converted by glycerol 3-phosphate dehydrogenase (GPDH) to dihydroxyacetone phosphate, which is then converted by triosephosphate isomerase (TPI) to D-glyceraldehyde-3-phosphate. This intermediate is reacted as formed with $^{32}P_i$ by means of glyceraldehyde-3-phosphate dehydrogenase (GAPDH). The resulting 1,3-diphosphoglycerate is reacted with the selected nucleoside diphosphate to produce the [γ-$^{32}$P]-nucleoside triphosphate with 3-phosphoglycerate kinase (PGK).

Since most of these commercially available enzymes, and especially the triosephosphate isomerase, are contaminated with myokinase (adenylate kinase), [β-$^{32}$P]-nucleoside triphosphate may also be produced. Thus, it is desirable to carry out the desired enzyme reactions under conditions which maximize the production of the [γ-$^{32}$P]-labeled produces and minimizes the concurrent production of [β-$^{32}$P]-products. Specificity of labeling is of great importance where the products are used for analytical determination, as in the assay of numerous protein kinases and in studies of nucleic acid structure and metabolism.

The [γ-$^{32}$P]-labeled products of high specific activity with minimal contamination with [β-$^{32}$P]-products are produced by limiting the enzyme concentrations so that the desired reactions are preferentially favored even though small amounts of myokinase may be present. The conversion enzymes GPDH, TPI, GAPDH, and PGK are used in amounts such that at least one and preferably all of them are present in concentrations within the range of 0.2 to 2.0 U/ml. In an optimized process, the concentrations of these reagents are not over 1.0 U/ml, such as the range from 0.3 to 0.9 U/ml.

In another preferred embodiment of the process, nicotinamide adenine dinucleotide (NAD+), which is required for two of the enzyme conversions, is continuously regenerated from its reduced form (NADH) by reaction with pyruvate in the presence of lactate dehydrogenase (LDH). The pyruvate is converted to lactate with the accompanying oxidation of NADH to NAD+.

REFERENCE TO DRAWING

The accompanying drawing (FIG. 1) is a schematic representations of the sequential enzymatic reaction process of this invention in preferred embodiment. The process can be used for preparing [γ-$^{32}$P]-ATP from ADP, as illustrated, or other [γ-$^{32}$P]nucleoside triphosphate (NTP) from the corresponding nucleoside diphosphate (NDP).

DETAILS OF PROCESS

The L-α-glycerophosphate (L-α-GP) can be added to the reaction substrate in admixture with D-α-glycerophosphate (D-α-GP). D-α-GP is stable and does not react. However, since pure L-α-GP is available commercially its use is preferred unless the L-D mixture is a less expensive source.

The other primary reactants are all commercially available; namely [$^{32}$P]-phosphate ($^{32}P_i$), and the nucleoside diphosphates (NDP). These diphosphates and the resulting triphosphates are summarized below:

| Diphosphate | Triphosphate |
| --- | --- |
| adenosine 5'diphosphate (ADP) | adenosine 5'triphosphate (ATP) |
| 2'-deoxyadenosine 5'-diphosphate (dATP) | 2'-deoxyadenosine 5'-triphosphate (dATP) |
| guanosine 5'-diphosphate (GDP) | guanosine 5'triphosphate (GTP) |
| inosine 5'diphosphate (IPP) | inosine 5'triphosphate (ITP) |
| adenyl 5'-yl-(α-β-methylene) diphosphate (AP(CH$_2$)P) | adenyl 5'-yl-(α-β-methylene) triphosphate (AP(CH$_2$)PP) |

The concentrations of the primary reactants are not critical. The following ranges are illustrative of the initial concentrations that can be used, the concentrations being given in micromoles per liter of reaction solution.

| Primary Reactant | Concentration (μM/l) |
| --- | --- |
| L-α-GP | 20–1000 |
| $^{32}P_i$ | 0.1–100 |
| NDP | 10–1000 |

It is desirable to have a sufficient amount of the L-α-GP to provide enough of the D-glyceraldehyde 3-phosphate for reaction with all of the $^{32}P_i$ without a large excess of the D-glyceraldehyde 3-phosphate being produced. On a stoichiometric basis from 2 to 20 times as much L-α-GP as the $^{32}P_i$ can be used advantageously. For example, 10 moles of L-α-GP can be used per mole of $^{32}P_i$.

NAD+ must also be present to participate in the conversion of L-α-GP to dihydroxyacetone phosphate by GPDH and in the conversion of D-glyceraldehyde 3-phosphate to 1,3-diphosphoglycerate by GAPDH, as represented in the accompanying schematic diagram (FIG. 1). The NAD+ is reduced to NADH. Therefore, since these reactions are reversible, the ratio of NAD+ to NADH must be kept high. This is accomplished preferentially by oxidation of the NADH formed back to NAD+. Oxidizing dyes such as phenazine methosulfate and/or thiazolyl blue, can be used. See J. Biol. Chem. 248, 8319–8321 (1973). However, it is preferable to regenerate the NAD+ by using pyruvate and lactate dehydrogenase (LDH) as represented in the schematic diagram of FIG. 1. The LDH in the presence of NADH and pyruvate forms lactate and NAD+. This mechanism for reconversion of the NAD+ is particularly desirable where the [γ-$^{32}$P] nucleoside triphosphate products are to be used directly as substrates for subsequent enzyme reactions without separation and recovery. Where the end products are simply the [γ-$^{32}$P]-nucleoside triphosphates, other means for regenerating the NAD+ can be used, or it may be possible that the NAD+ could be added in large excess. However, large excesses of NAD+ may be disadvantageous if it is desirable to achieve the highest possible specific activity of the [γ-$^{32}$P]NTP, due to contaminating unlabeled $P_i$, present in NAD+, that would dilute the specific activity.

In the preferred embodiment, the useable initial concentrations of the additional reactants are:

| Additional Reactant | Concentration |
| --- | --- |
| NAD+ | 50 –2000 M |
| Pyruvate | 500–5000 M |
| LDH | 1–10 U/ml |

The pyruvate can be added in salt form such as sodium or potassium pyruvate.

Commerically available enzymes may contain myokinase (MK) as a contaminant. Although commerical suppliers (e.g. BoehringerMannheim) give no level of MK contamination for GPDH, TPI, and GAPDH, and give for PGK and LDH a level of contamination of <0.01%, we have measured sufficient MK activity in each of these enzymes, especially TPI and GAPDH, to result in as much as 3% to 5% [β-$^{32}$P]labeling in the [γ-$^{32}$P]nucleoside triphosphate preparations. However, it has been discovered that the undesired reaction pathway (formation of [β-$^{32}$P]nucleoside triphosphate) can be minimized and the desired pathway preferentially favored by limiting the concentrations and balancing the activities of the conversion enzymes. The enzyme of lowest activity in the series can control the overall rate. In general, though it is preferable that all of the enzymes (GPDH, TPI, GAPDH, AND PGK) should be present in activities within the range of 0.2 to 2.0 International Units per milliliter (ml) of reaction solution. A unit (International Activity Standard) is defined as the enzyme activity required to transform 1 micromole of substrate per minute under optimal conditions. Preferably, at least one, and, optimally, all of the conversion enzymes are limited to activities of not over 2 U/ml, such as 0.2 to 1.0 U/ml. For example, the following concentrations have been found effective:

| Enzyme | Concentration (U/ml) |
| --- | --- |
| GPDH | 0.60 |
| TPI | 0.50 |
| GAPDH | 0.80 |
| PGK | 0.45 |

The LDH enzyme is desirably present in relatively larger amounts than the conversion enzymes, such as 2.0 to 4.0 U/ml). The pyruvate is also present in excess.

In general, the enzymatic reactions are conducted under conditions of pH, temperature and enzyme stability which are suitable for the enzymes involved. These conditions are per se well known. A magnesium source is added such as $MgCl_2$ to provide $Mg^{++}$, for example, in amounts of 2 to 20 mM (viz. 12 mM). Enzyme stabilizers such as cysteine and dithiothreitol are desirable. For example, cysteine can be advantageously added in an amount of 2 to 10 mM (viz. 4 mM); and also dithiothreitol in an amount of 2 to 10 mM (viz. 6 mM). The reactions may be conducted at room temperatures (20°–25°), but temperatures from about 15° to 40° C. could be used. The only advantage in departing from the ambient conditions is that the overall reaction rate could be increased or decreased. The reactions can take place in the range of about pH 7.0 to 9.5. However, if the [γ-$^{32}$P]nucleoside triphosphate is to be used as substrate for subsequent enzyme reactions, for example the use of [γ-$^{32}$P]ATP and polynucleotide kinase to make [5′-$^{32}$P]-3′ADP, it may be desirable to run the first reactions at a pH that is optimal for the second enzyme step (e.g. pH 9.0 for the polynucleotide kinase).

Under the conditions described, the reactions proceed rapidly. Depending on the amount of the $^{32}P_i$ to be incorporated in the nucleoside diphosphate, and the other conditions used, the reactions may be completed with substantial incorporation (≧95%) of the $^{32}P_i$ in from 10 to 30 minutes. Under some conditions and to assure completion, the reactants can be held for longer times up to 1 to 2 hours. If desired the progress of the $^{32}P_i$ utilization can be followed by monitoring the amount of radioactivity which becomes adsorbable on Norit A with time. A very small aliquot (50–100 nl) of the reaction mixture is removed by dipping into it an end of a piece of surgical silk string. The string is then dipped into 1 ml of 50 mM $KH_2PO_4$ and a 25 μl aliquot is withdrawn for liquid scintillation counting. A spatula full of Norit A (50 to 100 mg) is then added to the remainder of the $KH_2PO_4$ solution. After mixing, and then separating the Norit A by centrifugation, a second 25 μl aliquot of the supernatant fluid is taken for liquid scintillation counting. The radioactivity in the first 25 μl aliquot (before Norit A) is used to determine total radioactivity in the string-derived aliquot and the radioactivity in the second 25 μl aliquot (after Norit A) used to determine radioactivity remaining as $^{32}P_i$ only. The difference between the two values represents Norit A adsorbable radioactivity.

On completion, the [γ-$^{32}$P]nucleoside triphosphate can be recovered and purified or further reacted, for example, to produce other [$^{32}$P]-labeled substances. The [γ-$^{32}$P]-products such as [γ-$^{32}$P]ATP, -deoxy ATP, etc. may be separated from the reaction mixture and recovered by known chromatographic procedures. An example of such a procedure could be the use of anion exchange chromatography (e.g. Dowex 1 or DEAE-Sephadex, Cl⁻ form). The sample may be applied to a column of such material and the purified product may be preferentially eluted by a continuous or discontinuous gradient of increasing salt concentration.

The recovered [γ-$^{32}$P]nucleoside triphosphates are useful as analytical reagents. [γ-$^{32}$P] is typically used for the assay of cAMP-dependent protein kinases and a variety of other kinases (e.g. Schlender, K. K., and Reimann, E. M. (1977) J. Biol. Chem. 252, 2384–2389) and for the assay of various ATPases (e.g. Sugino, Y., and Miyoshi, Y. (1964) J. Biol. Chem. 239, 2360–2364). [γ-$^{32}$P]GTP can be used to assay hormone-sensitive GTPase (Cassel, D., and Selinger, Z. (1977) J. Cyclic Nucleotide Res. 3, 11–22), and for labeling the 5′-terimus of ribonucleic acid (e.g. Banerjee, A. K., Eoyang, L., Hori, K., and August, J. T. (1967) Proc. Nat. Acad. Sci. USA 57, 986–993). [γ-$^{32}$P]dATP, [γ-$^{32}$P]ITP, and [γ-$^{32}$P]AP(CH$_2$)PP can be used for determining substrate specificity of a variety of enzymes involved in phosphate-transfer reactions. We have used [γ-$^{32}$P]AP(CH$_2$)PP as substrate for cAMP-dependent protein kinase and this compound has the additional advantage that it cannot be readily hydrolyzed between the α- and β-phosphates by phosphohydrolases.

This invention is further illustrated by the following specific examples.

EXAMPLE I

A. Synthesis of [γ-$^{32}$P]ATP from $^{32}P_i$. $^{32}P_i$ is incorporated into [γ-$^{32}$P]ATP by the reactions shown in FIG. 1. The volume in which the $^{32}P_i$ is purchased essentially dictates the reagent and enzyme volumes which are added in the ratios below.

| | |
|---|---|
| 0.5 volume | $^{32}P_i$ + H$_2$O |
| 0.4 volume | "Stage I reagent mixture" (see Table II) |
| 0.1 volume | "enzyme-cysteine mix" (Table I and text) |
| 1.0 volume | |

The final concentrations of enzymes and reagents are shown in Tables I and II. Immediately following the addition of the "reagent mixture" an aliquot is taken from the reaction vessel by the string technique (described above) to determine the initial (zero time) amount of charcoal adsorbable radioactivity. Once this aliquot has been taken the reaction is initiated by the addition of the "enzyme-cysteine mix". The reaction is allowed to proceed at room temperature until 95% or more of the $^{32}P_i$ has been incorporated into [γ-$^{32}$P]ATP, i.e. charcoal adsorbable material. Progress of the reaction is monitored at 5 or 10 min intervals, usually up to about 30 min, by the string aliquot technique. The reaction is terminated by setting the reaction vessel for 10 min into water that had just been brought to a boil.

B. Enzyme-cysteine mix. To assure a successful preparation of [γ-$^{32}$P]ATP the "enzyme-cysteine mix" should be prepared immediately before its use to initiate the reaction. A 15 μl aliquot of the stock mixture of enzymes (see Table I) is centrifuged in a 6×50 mm disposable culture tube in an appropriate centrifuge adapter at 16,000×g for 15 min. The supernatant fraction is discarded and the enzyme-containing pellet is then dissolved in 15 μl of 50 mM Tris-Cl, pH 9.0. This centrifugation is done to remove most of the (NH$_4$)$_2$SO$_4$ since L-α-glycerolphosphate dehydrogenase is reported to be inhibited by sulfate. During this centrifugation a 60 mM solution of cysteine-HCl is freshly prepared (47.3 mg per 5 ml) and is neutralized to about pH 7.5 to pH 8.0 by the addition of crystalline Tris base. The "enzyme-cysteine mix" is then prepared by combining 5 μl of the centrifuged and redissolved enzyme mixture, 7 μl of 500 mM Tris-Cl, pH 9.0, 46.7 μl of 60 mM cysteine-HCl, and 11.3 μl of water to a final volume of 70 μl.

C. Purification of ATP. The [γ-$^{32}$P]ATP is purified by anion exchange chromatography. Of several systems we have tried, we find most convenient the use of the last two steps of the procedure described by Nakai and Brooker (1975, Biochim. Biophys. Acta 391, 222–239). The sample (contents of the reaction vessel) is applied and allowed to run into a 0.7×4 cm column of Dowex 1 (BioRad AG 1-X4, 200–400 mesh, Cl⁻ form) or DEAE-Sephadex (Pharmacia, A-25, Cl⁻ form) that is run at 4° and was previously washed with about 30 ml of water. The reaction vessel is then rinsed out two times with 1 ml of H$_2$O and one time with 1 ml of 30 mM HCl. These rinses are successively applied to the column and allowed to run in. The column is then washed with 30 ml of 30 mM HCl to remove inorganic phosphate, AMP, and ADP. The specifically labeled ATP is then eluted with 250 mM HCl. One ml fractions are collected in plastic test tubes and the $^{32}$P-labeled ATP appears in the first 5 to 7 ml of the 250 mM HCl eluate. The ATP peak is pooled and neutralized by adding NaOH or Tris-base. The neutralized ATP is then stored at −70° in 0.5 to 1 ml aliquots in plastic vials.

D. Quantitative evaluation by thin-layer chromatography. In addition to the charcoal-adsorption method, the procedure may be monitored quantitatively by thin-layer chromatography and analysis of the chromatograms by radioactivity scans. Samples of the reaction are withdrawn by the string technique and the string is dipped into 200 μl of 50 mM KH$_2$PO$_4$. One μl aliquots of these solutions are then spotted on 1×20 cm channels on PEI-cellulose plates (20×20 cm) prewashed with water. Once samples from the various stages of the procedure have been spotted, the plates are developed by the one-dimensional system described by Gonzales and Geel (1975, Anal. Biochem. 63, 410–413). The plates are first developed 6 cm in 2 M sodium formate, pH 3.4, and then are transferred immediately (wet) to continue developing to 16–18 cm in 4 M sodium formate, pH 3.4. After drying, the plates are exposed to X-ray film for radioautography. The thin-layer plates are then cut into the respective channels and the distribution of radioactivity into the various reaction products is determined on a strip-scanner adapted for thin-layer chromatography plates. Alternatively, the areas on the respective channels corresponding to the various reaction products, identified by comparison with the radioautograph, can be cut out and the radioactivity determined by liquid scintillation spectrometry.

TABLE I

Enzymes

| Enzyme[a] | Stock[b] Mixture | | Enzyme-Cysteine Mixture[c] | Final Concentration in Stage I Reaction | |
|---|---|---|---|---|---|
| | µl | mg/ml | µg/ml | µg/ml | U/ml[d] |
| Glycerolphosphate dehydrogenase; Rabbit muscle; 60 U/mg; 2 mg/ml | 100 | 1.4 | 100 | 10 | 0.60 |
| Triosephosphate isomerase; Rabbit muscle; 5000 U/mg; 2 mg/ml | 1 | 0.014 | 1 | 0.1 | 0.50 |
| Glyceraldehyde-3-P dehydrogenase; Rabbit muscle; 80 U/mg; 10 mg/ml | 20 | 1.4 | 100 | 10 | 0.80 |
| 3-Phosphoglycerate kinase; Yeast; 450 U/mg; 10 mg/ml | 2 | 0.14 | 10 | 1 | 0.45 |
| Lactate dehydrogenase; Rabbit muscle; 550 U/mg; 5 mg/ml | 20 | 0.70 | 50 | 5 | 2.75 |
| | 143 µl | | | | |

[a] All of these enzymes are obtained as suspensions in 3.2 M (NH$_4$)$_2$SO$_4$ from Boehringer-Mannheim Biochemicals, 7941 Castleway Drive, P.O. Box 50816, Indianapolis, Indiana 46250.
[b] The indicated volumes of the respective enzymes are mixed in a 0.5 ml plastic V-tube and stored as a stock mixture (143 µl) in the refrigerator. A 15 µl aliquot of this mixture is then used for each preparation.
[c] The "enzyme-cysteine mix" comprises the above enzymes at the concentrations indicated in 40 mM cysteine and 50 mM Tris-Cl, pH 9.0 (see text).
[d] Enzyme activities are based on data provided by the manufacturer.

TABLE II

Reagent Mixture

| Reagent and Stock Concentration | | | Volume Used | Final Concentration in Reaction |
|---|---|---|---|---|
| | | | µl | mM |
| Tris-Cl, pH 9.0 | 500 | mM | 50 | 50 |
| MgCl$_2$ | 300 | mM | 20 | 12 |
| Dithiothreitol | 100 | mM | 30 | 6 |
| L-α-glycerolphosphate | 2.4 | mM | 25 | 0.12 |
| βNAD+ | 10 | mM | 25 | 0.5 |
| ADP (fresh)[a] | 2 | mM | 12.5 | 0.05 |
| Pyruvate (Na) (fresh)[a] | 40 | mM | 12.5 | 1 |
| Water | | | 25 | |
| | | | 200 µl | |

[a] All reagents are stored as frozen stock solutions except ADP and pyruvate which are prepared freshly for each preparation. Neither Na-ADP nor Na-pyruvate need to be neutralized prior to adding to the Reagent Mixture for the reaction. If it is not necessary to obtain the highest isotope specific activity possible, the ADP may also be stored conveniently as a frozen stock solution. On the other hand, if the highest possible specific activity is desired, the ADP should be chromatographically purified free of P$_i$ prior to use. All reagents are obtained from Boehringer-Mannheim Biochemicals (see Table 1) except Tris-Cl, MgCl$_2$ and charcoal (Norit A) which are available from Fischer Scientific, 711 Forbes Avenues, Pittsburgh, Pennsylvania 15219.

EXAMPLE II

Synthesis of [γ-$^{32}$P]dATP for $^{32}$P$_i$. This preparation proceeds exactly as that described above for [γ-$^{32}$P]ATP in Example I, except that 2'deoxy ADP is substituted for the ADP. Otherwise monitoring the reaction and purification of the final product are accomplished by the same techniques described under Example I.

EXAMPLE III

Synthesis of [γ-$^{32}$P]GTP from $^{32}$P$_i$. This preparation proceeds exactly as that described above for [γ-$^{32}$P]ATP in Example I, except that GDP is substituted for the ADP. Otherwise monitoring the reaction and purification of the final product are accomplished by the same techniques described under Example I.

EXAMPLE IV

Synthesis of [γ-$^{32}$P]ITP from $^{32}$P$_i$. This preparation proceeds exactly as that described above for [γ-$^{32}$P]ATP in Example I, except that IDP is substituted for the ADP. Otherwise monitoring the reaction and purification of the final product are accomplished by the same techniques described under Example I.

EXAMPLE V

Synthesis of [γ-$^{32}$P]AP(CH$_2$)PP from $^{32}$P$_i$. This preparation proceeds exactly as that described above for [γ-$^{32}$P]ATP in Example I, except that AP(CH$_2$)P is substituted for the ADP. Otherwise monitoring the reaction and purification of the final product are accomplished by the same techniques described under Example I.

We claim:

1. An enzymatic process for preparing gamma [$^{32}$P]-labeled nucleoside triphosphates comprising:
   (a) forming a reaction mixture in aqueous solution containing as the primary reactants L-α-glycerophosphate (L-α-GP), [$^{32}$P]-phosphate ($^{32}$P$_i$), and a nucleoside diphosphate (NDP) selected from the class consisting of adenosine 5'diphosphate (ADP), 2'-deoxyadenosine 5'-diphosphate (dADP), guanosine 5'diphosphate (GDP), inosine 5'diphosphate (IDP), and adenyl 5'-yl-(α-β-methylene) diphosphate AP(CH$_2$)P;
   (b) subjecting said primary reactants to enzymatic reactions in the presence of the conversion enzymes glycerol 3-phosphate dehydrogenase (GPDH), triosephosphate isomerose (TPI), glyceraldehyde 3-phosphate dehydrogenase (GAPDH), and 3-phosphoglycerate kinase (PGK); and
   (c) also having present in said solution during said reactions nicotinamide adenine dinucleotide (NAD+) together with pyruvate and lactate dehydrogenase (LDH) to reconvert the reduced form of nicotinamide adenine dinucleotide (NADH) to NAD+.

2. The process of claim 1 in which the conversion enzymes as added to the reaction solution may contain myokinase (MK) as a contaminant, and in which the activities of said conversion enzymes are balanced and each limited to an activity in the reaction solution within the range from 0.2 to 2.0 International Activity Units per milliliter (U/ml).

3. The process of claim 1 or claim 2 in which said NDP is ADP.

4. The process of claim 1 or claim 2 in which said NDP is dADP.

5. The process of claim 1 or claim 2 in which said NDP is GDP.

6. The process of claim 1 or claim 2 in which said NDP is IDP.

7. The process of claim 1 or claim 2 in which said NDP is AP(CH$_2$)P.

8. The process of claim 2 in which at least one of said concentrations of said conversions enzymes is limited to not over 1.0 U/ml.

9. An enzymatic process for preparing gamma [$^{32}$P]-labeled nucleoside triphosphate comprising:
   (a) forming a reaction mixture in aqueous solution containing as the primary reactants L-α-glycerophosphate (L-α-GP), [$^{32}$P]-phosphate ($^{32}$P$_i$), and a nucleoside diphosphate (NDP) selected from the class consisting of adenosine 5'diphosphate (ADP), 2'-deoxyadenosine 5'-diphosphate (dADP), guanosine 5'diphosphate (GDP), inosine 5'diphosphate (IDP), and adenyl 5'-yl-(α-β-methylene) diphosphate AP(CH$_2$)P;

(b) subjecting said primary reactants to enzymatic reactions in the presence of the conversion enzymes glycerol 3-phosphate dehydrogenase (GPDH), triose phosphate isomerase (TPI), glyceraldehyde 3-phosphate dehydrogenase (GAPDH), and 3-phosphoglycerate kinase (PGK); and (c) also having present in said solution during said enzymatic reactions nucotinamide adenine dinucleotide (NAD+) in sufficient amount to permit the essentially quantitative conversion both of L-α-glycerophosphate to dihydroxyacetone phosphate by GPDH and the conversion of D-glyceraldehyde 3-phosphate to 1,3-diphosphoglycerate by GAPDH.

10. The process of claim 9 in which the conversion enzymes as added to the reaction solution may contain myokinase (MK) as a contaminant, and in which the activities of said conversions enzymes are balanced and each limited to an activity in the reaction solution within the range from 0.2 to 2.0 International Activity Units per milliliter (U/ml).

11. To process of claim 9 or 10 in which said NDP is ADP.

12. The process of claim 9 or 10 in which said NDP is dADP.

13. The process of claim 9 or claim 10 in which said NDP is GDP.

14. The process of claim 9 or claim 10 in which said NDP is IDP.

15. The process of claim 9 or claim 10 in which said NDP is AP(CH$_2$)P.

16. The process of claim 10 in which at least one of said conversions enzymes is limited to not over 1.0 U/ml.

* * * * *